(12) United States Patent
Whiteley

(10) Patent No.: US 11,596,473 B2
(45) Date of Patent: Mar. 7, 2023

(54) MEDICAL DEVICE FOR TREATING A VEIN

(71) Applicant: Mark Whiteley, Guildford (GB)

(72) Inventor: Mark Whiteley, Guildford (GB)

(73) Assignee: Mark Steven Whiteley, Guildford (GB)

( * ) Notice: Subject to any disclaimer, the term of this patent is extended or adjusted under 35 U.S.C. 154(b) by 257 days.

(21) Appl. No.: 17/116,768

(22) Filed: Dec. 9, 2020

(65) Prior Publication Data

US 2021/0085391 A1 Mar. 25, 2021

Related U.S. Application Data

(62) Division of application No. 15/539,500, filed as application No. PCT/GB2015/054016 on Dec. 15, 2015, now Pat. No. 11,039,881.

(30) Foreign Application Priority Data

Dec. 23, 2014 (GB) .................................... 1423024
Jul. 2, 2015 (GB) .................................... 1511595

(51) Int. Cl.
*A61B 18/14* (2006.01)
*A61B 18/08* (2006.01)
(Continued)

(52) U.S. Cl.
CPC .... *A61B 18/1492* (2013.01); *A61B 17/00491* (2013.01); *A61B 18/08* (2013.01);
(Continued)

(58) Field of Classification Search
CPC . A61B 18/1492; A61B 18/1815; A61B 18/08; A61B 18/24; A61B 2018/00589; A61B 2018/00279; A61B 2018/00267; A61B 2018/1475; A61B 2018/0022; A61B 2018/00404; A61B 2018/048;
(Continued)

(56) References Cited

U.S. PATENT DOCUMENTS 4,581,017 A * 4/1986 Sahota ............... A61M 25/1002
606/192
4,878,495 A * 11/1989 Grayzel ............. A61M 25/1011
606/193

(Continued)

FOREIGN PATENT DOCUMENTS

FR 2811541 A3 * 1/2002 ......... A61B 18/1492
JP 4187931 B2 * 11/2008 ......... A61B 18/1492
WO WO-2012/071058 A1 5/2012

OTHER PUBLICATIONS

International Search Report and Written Opinion for International Application No. PCT/GB2015/054016, dated Jun. 20, 2016.

*Primary Examiner* — Nathan R Price
*Assistant Examiner* — Mark A Igel
(74) *Attorney, Agent, or Firm* — Marshall, Gerstein & Borun LLP

(57) ABSTRACT

A medical device for treating a vein, including component parts thereof, wherein the device comprises a vein stretching member; a vein stretching member for use with the device; a kit of parts including the device and one or more vein stretching member and a method for treating a vein including use of the device.

17 Claims, 11 Drawing Sheets

Figure 1:
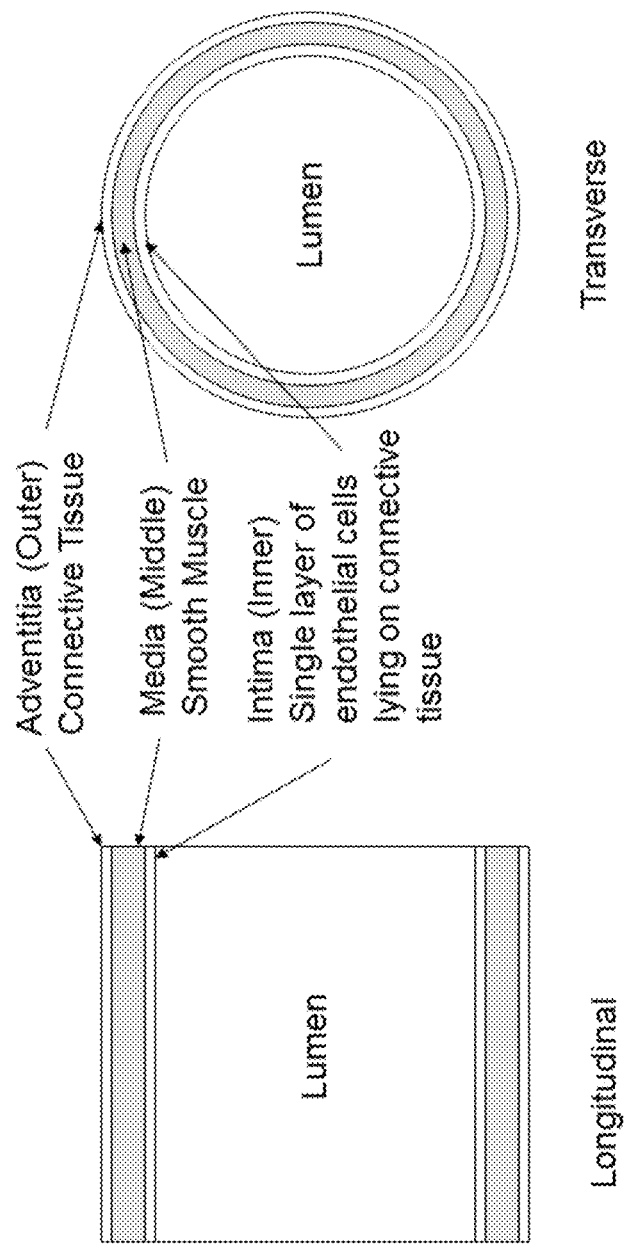

(51) Int. Cl.
*A61B 18/24* (2006.01)
*A61M 25/00* (2006.01)
*A61B 18/18* (2006.01)
*A61B 18/00* (2006.01)
*A61B 18/04* (2006.01)
*A61B 17/00* (2006.01)
*A61M 29/02* (2006.01)

(52) U.S. Cl.
CPC .......... *A61B 18/1815* (2013.01); *A61B 18/24* (2013.01); *A61M 25/0082* (2013.01); *A61M 29/02* (2013.01); *A61B 2018/0022* (2013.01); *A61B 2018/00267* (2013.01); *A61B 2018/00279* (2013.01); *A61B 2018/00404* (2013.01); *A61B 2018/00577* (2013.01); *A61B 2018/00589* (2013.01); *A61B 2018/048* (2013.01); *A61B 2018/1475* (2013.01); *A61B 2018/1861* (2013.01); *A61M 25/0074* (2013.01); *A61M 2025/0096* (2013.01)

(58) Field of Classification Search
CPC .. A61B 2018/00577; A61B 2018/1861; A61B 17/00491; A61M 29/02; A61M 2025/0096; A61M 25/0082; A61M 25/0074
See application file for complete search history.

(56) References Cited

U.S. PATENT DOCUMENTS

| | | | | | |
|---|---|---|---|---|---|
| 4,896,669 | A * | 1/1990 | Bhate | ............... | A61M 25/1006 604/917 |
| 4,994,072 | A * | 2/1991 | Bhate | ............... | A61M 25/1038 604/917 |
| 5,160,321 | A * | 11/1992 | Sahota | ............... | A61M 25/1002 604/101.02 |
| 5,196,024 | A * | 3/1993 | Barath | ........... | A61B 17/320725 606/191 |
| 5,226,887 | A * | 7/1993 | Farr | ................. | A61M 25/1027 604/103.09 |
| 5,295,995 | A * | 3/1994 | Kleiman | ............ | A61M 25/104 604/103.07 |
| 5,308,356 | A * | 5/1994 | Blackshear, Jr. | . | A61M 25/1002 606/194 |
| 5,318,587 | A * | 6/1994 | Davey | ............... | A61M 25/1038 604/103.14 |
| 5,320,634 | A * | 6/1994 | Vigil | ............. | A61B 17/320725 604/103.08 |
| 5,336,234 | A * | 8/1994 | Vigil | ................... | A61M 25/104 606/171 |
| 5,433,706 | A * | 7/1995 | Abiuso | ............. | A61M 25/1002 604/101.01 |
| 5,456,667 | A * | 10/1995 | Ham | .................... | A61M 29/02 606/198 |
| 5,458,572 | A * | 10/1995 | Campbell | ........... | A61M 25/104 604/103.08 |
| 5,490,839 | A * | 2/1996 | Wang | ................ | A61M 25/1038 604/103 |
| 5,545,132 | A * | 8/1996 | Fagan | ............. | A61M 25/1002 604/103.08 |
| 5,645,529 | A * | 7/1997 | Fagan | ................ | A61M 25/1011 604/101.01 |
| 5,693,014 | A * | 12/1997 | Abele | ............... | A61M 25/1002 604/103.08 |
| 5,704,913 | A * | 1/1998 | Abele | .................. | A61M 25/104 604/101.02 |
| 5,746,745 | A * | 5/1998 | Abele | ............... | A61M 25/1002 604/103.08 |
| 5,868,708 | A * | 2/1999 | Hart | .................. | A61M 25/1002 604/107 |
| 5,882,329 | A * | 3/1999 | Patterson | ........... | A61B 17/3207 604/523 |
| 5,893,868 | A * | 4/1999 | Hanson | ................. | A61F 2/0095 606/198 |
| 6,033,397 | A * | 3/2000 | Laufer | ............... | A61B 18/1492 604/113 |
| 6,074,338 | A * | 6/2000 | Popowski | ............ | A61N 5/1002 600/3 |
| 6,146,396 | A * | 11/2000 | Konya | ................ | A61B 17/221 606/159 |
| 6,159,196 | A * | 12/2000 | Ruiz | ..................... | A61M 25/00 604/500 |
| 6,165,172 | A * | 12/2000 | Farley | ............. | A61B 18/1492 606/49 |
| 6,338,709 | B1 * | 1/2002 | Geoffrion | ............ | A61N 5/1002 600/3 |
| 6,458,139 | B1 * | 10/2002 | Palmer | ................. | A61B 17/221 606/113 |
| 6,511,496 | B1 * | 1/2003 | Huter | ..................... | A61F 2/0108 606/200 |
| 6,551,303 | B1 * | 4/2003 | Van Tassel | ......... | A61B 17/0057 604/104 |
| 6,652,556 | B1 * | 11/2003 | VanTassel | ............. | A61F 2/0105 606/200 |
| 7,252,650 | B1 * | 8/2007 | Andrews | ................. | A61F 2/958 604/103.09 |
| 9,060,802 | B2 * | 6/2015 | Kugler | .................... | A61M 25/10 |
| 9,339,291 | B2 * | 5/2016 | Aggerholm | ........... | B29C 59/021 |
| 10,052,462 | B2 * | 8/2018 | Belafsky | ............ | A61M 25/1011 |
| 2002/0161388 | A1 * | 10/2002 | Samuels | ................ | A61M 25/10 428/36.9 |
| 2002/0183777 | A1 * | 12/2002 | Shannon | ............. | A61M 25/104 606/192 |
| 2004/0243201 | A1 * | 12/2004 | Goldman | ......... | G02F 1/134363 607/101 |
| 2005/0177105 | A1 * | 8/2005 | Shalev | ................ | A61M 27/008 604/104 |
| 2005/0288629 | A1 * | 12/2005 | Kunis | .................... | A61M 25/10 604/22 |
| 2007/0282359 | A1 | 12/2007 | Tal | | |
| 2008/0183132 | A1 * | 7/2008 | Davies | ................ | A61M 25/104 604/103.09 |
| 2008/0243102 | A1 | 10/2008 | Lary | | |
| 2009/0030370 | A1 * | 1/2009 | Nishtala | ................ | A61M 25/04 604/544 |
| 2009/0287203 | A1 * | 11/2009 | Mazzone | .......... | A61M 25/1006 606/21 |
| 2011/0046543 | A1 | 2/2011 | Brandeis | | |
| 2013/0310823 | A1 * | 11/2013 | Gelfand | ........... | A61M 25/0082 606/41 |
| 2014/0142598 | A1 * | 5/2014 | Fulton, III | ...... | A61B 17/320725 606/159 |
| 2015/0343178 | A1 * | 12/2015 | Fulton, III | ............ | A61M 25/04 604/509 |
| 2018/0014879 | A1 | 1/2018 | Whiteley | | |

* cited by examiner

MEDICAL DEVICE FOR TREATING A VEIN

CROSS-REFERENCE TO RELATED APPLICATION

This is a divisional of U.S. patent application Ser. No. 15/539,500, filed Jun. 23, 2017, which is the US National Phase of International Patent Application No. PCT/GB2015/054016, filed Dec. 15, 2015, which claims priority to United Kingdom Application Nos. 1423024.7, filed Dec. 23, 2014, and 1511595.9, filed Jul. 2, 2015. The disclosures of U.S. Ser. No. 15/539,500, PCT/GB2015/054016, GB 1423024.7, and GB1511595.9 are hereby incorporated by reference in their entirety.

FIELD OF THE INVENTION

The invention relates to a medical device for treating a vein, including component parts thereof, wherein said device comprises a vein stretching member; a vein stretching member for use with said device; a kit of parts comprising said device and one or more vein stretching members and a method for treating a vein comprising use of said device.

BACKGROUND OF THE INVENTION

Veins are an aspect of the vascular system, a network of blood vessels that function to distribute blood around the body. Their primary function is to return blood back to the heart, with the exception of the portal veins that distribute blood between capillary beds. Veins are essentially hollow tubes that typically comprise three distinct cell layers which collapse in the absence of blood. Importantly, veins possess one-way valves periodically distributed along their length to ensure the uni-directional flow of blood to the heart. This process of blood flow is assisted by the thoracic pump action of breathing during respiration, and the skeletal-muscle pump, a collection of skeletal muscles that upon contraction increase venous return to the heart. In between muscle contractions, intramuscular pressure transiently returns to a level below the venous blood pressure. This results in blood from the capillary system refilling the veins until the next contraction.

Veins are classified in a number of ways, such as according to their size, location, and the aspect of the circulatory system to which they belong. In the legs there are three main categories: superficial veins, communicating veins, and deep veins. Superficial veins lie close to the body surface with no corresponding arteries, and, in the legs, carry about 10 to 15 percent of the blood. Superficial veins drain into communicating veins, which themselves drain into deep veins. Deep veins are intra-muscular and carry 85 to 90 percent of the blood back to the heart.

If the walls of the veins become weakened or damaged as a consequence of age or injury, or the valves become stretched or fail due to genetic or familial factors, blood may begin to leak backward or flow in both directions. This reverse flow creates abnormal flow and pressure profiles in the veins, resulting in pathological stretching and dilating. The resulting abnormal veins and distended veins are one form of venous disease called "varicose veins".

Venous diseases are most commonly manifested as venous insufficiency, or varicose veins. Venous reflux disease leading to varicose veins or other signs and symptoms of chronic venous incompetence (CVI) affect some 30 to 40% of the adult population in Western societies. Varicose veins are most common in the superficial veins of the leg. Spider veins are a small unsightly type of abnormal vein, which are often painless and only a cosmetic concern as their function is not essential to the venous system. However, if larger or more important veins become dysfunctional this can have more serious consequences. As these vessels enlarge, they often become more dilated and tortuous leading to discomfort, aching, and itching. Occasionally burning and throbbing occurs in the muscles as blood pools or backs up in the tissue. As the veins become more abnormal they may begin to leak into the surrounding tissue resulting in oedema. Prolonged disease can often result in chronic venous insufficiency, due to blood pooling, clot formation and repeated inflammation. As this condition worsens, skin damage and inflammation ensues and the skin eventually turns a reddish brown and is accompanied by a hard and itchy epidermis. When venous disease becomes severe, venous stasis ulcers occur on the skin where a reduction in venous blood flow causes changes in skin pressure and tissue oxygen levels. Furthermore, thrombophlebitis may result where formation of a blood clot results in inflammation. These changes may occur in the superficial veins, where they are painful, or more seriously in deep veins (deep vein thrombosis or DVT) where the clot can dislodge resulting in a distal embolism elsewhere in the body, often with fatal consequences (pulmonary embolism or PE).

Several surgical and nonsurgical treatment options, or combinations of options, are available for the various types of venous diseases all aimed at reducing symptoms and the risk of further complications.

Non-surgically, the discomfort of both leg swelling and leg pain can be improved with compression stockings, and often also involves combinational therapy with prescription drugs (e.g. anticoagulants if there are clots present) and anti-inflammatory medication. Other nonsurgical techniques for the treatment of patients with CVI, with or without visible varicose veins, is that of endovenous surgery. As the name implies, it involves treating incompetent veins from within such as by sclerotherapy and endovenous thermal ablation. Endovenous surgery with thermal ablation to ablate incompetent venous trunks has now become the preferred treatment for varicose veins and other conditions caused by venous reflux in the leg (NICE CG 168, July 2013). In the leg, these veins include: the Great Saphenous Vein (GSV); Small Saphenous Vein (SSV); and the Anterior Accessory Saphenous Vein (AASV). In pelvic venous reflux disease, veins that require ablation include: the Gonadal Veins; and Internal Iliac Veins and some of their tributaries including the obturator veins and rectal veins. In the arms and hands, increasingly patients are requesting treatment of prominent veins including: Cephalic Veins; Basilic Veins; and Veins on the dorsum of the hands Endovenous thermal ablation (laser and radiofrequency treatment or ablation) is a minimally invasive ultrasound-guided technique for treating varicose veins using laser energy (laser) or electrical current alternating at radiofrequency rates (radiofrequency). The process for endovenous laser treatment involves passing an optical fibre into a diseased vein, shining laser light into the interior of the vein which destroys the vein and it is removed by a process of fibrosis. Similarly, radiofrequency ablation of veins involves using heat generated by a high frequency alternating current to shrink and destroy veins. When sufficient heat has passed into the vein the whole of the vein wall is ablated. In essence this means that all the cells of the vein wall are destroyed by the heat as the proteins coagulate and the protein structure of the vein wall is denatured. It is important that carbonisation is avoided as if too much heat is passed too quickly into the vein wall, the inner aspect may change from coagulated protein to carbon, destroying the integrity of the inside of the vein and creating a thrombogenic surface. This, in addition to damage to living cells deeper in the vein wall, can also result in a thrombus that can re-cannulate and cause recurrent varicose veins.

Endovenous thermal ablation requires the use of tumescence (or "tumescent anaesthesia"). This entails injecting a fluid around the outside of the vein to be treated and separating the vein from surrounding tissue. It provides three main actions. The first is to use the volume of the fluid as a thermal barrier, preventing heat that is being used to ablate the vein wall from damaging the surrounding tissues. The second is to anaesthetise the vein wall and surrounding tissues. The third is to cause venospasm, making the vein constrict tightly onto the endovenous device thus increasing contact between the vein and device and expelling any blood surrounding the endovenous device.

In view of the success of the endovenous approach, both in terms of the minimally invasive nature, low post-operative pain, minimal scars as well as permanent ablation when performed correctly, focus has turned on trying to develop alternative endovenous techniques that provide the same advantages and results as the catheter based endovenous thermoablation but without the need for tumescence.

The first of these, and pre-dating the thermoablation techniques, is sclerotherapy and in particular foam sclerotherapy. Sclerotherapy is the injection of a liquid into a vein that causes the vein to become inflamed and destroyed. The most commonly used sclerosants are detergent sclerosants such as sodium tetradecyl sulphate (STS) and polidocanol (POL). Other sclerosants used are hypertonic saline, glycine and chromate, although the numbers of patients treated with these in most practices is exceptionally small. Sclerotherapy is often the treatment of choice for telangiectasiae (spider veins) or other veins following surgery.

Other non-tumescent techniques include mechanochemical ablation (MOCA) and glue. MOCA is a combination of a mechanical device and sclerotherapy. The mechanical component involves a rotating wire that damages the inner aspect of the vein wall in order to make the sclerosant more effective in ablating the target vein. Initially this was thought to be due to an increased damage profile to the inner surface of the vein, although more recent research has suggested that it works by increasing the penetration of the sclerosant into the vein wall. The glue device involves the injection of a cyanoacrylate glue into the lumen of the target vein. In the short term, the vein wall is stuck together ablating the vein. In the longer term, histological studies have suggested that as the glue is broken down a foreign body reaction results and fibrose healing occurs in the vein lumen.

In summary, current techniques involve the delivery of ablation energy, sclerosants or glue to the lumen and internal wall of a blood vessel. Research has suggested that to achieve permanent ablation of a vein wall, each of the 3 layers of the vein wall must be ablated (FIG. 1). However, using all existing techniques we have observed an inherent physiological problem when undertaking ablation.

Figure 2:
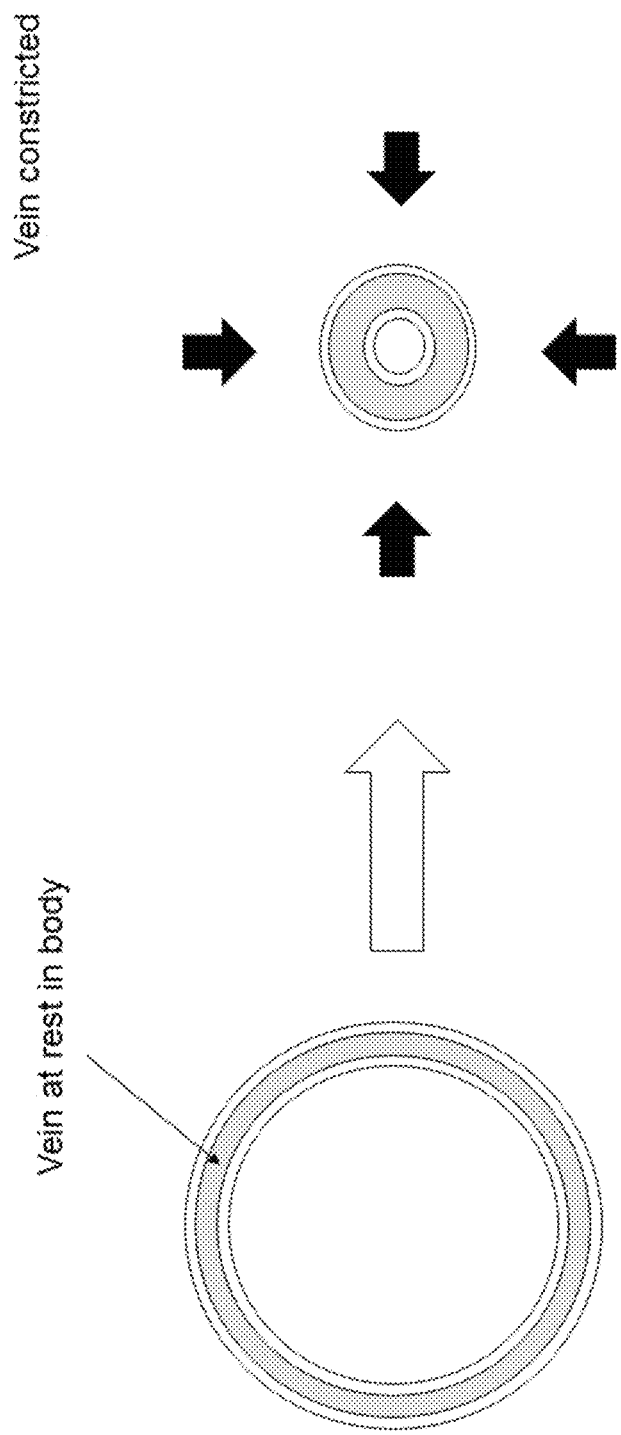

In the context of endovenous thermoablation, when a tumescent fluid is injected around the vein it acts as vasoconstrictor, typically causing constriction of the vein onto the endovenous device (FIG. 2). Whilst this constriction ensures optimal contact between the vein wall and the endovenous device and also excludes blood, allowing maximum transfer of energy from the endovenous device and into the vein wall, constriction of the vein causes the vein wall to thicken. This causes heat conduction problems through the vein wall and one has to be careful not to carbonise the inner layer of the vein (intima).

Likewise in sclerotherapy treatment, the sclerosant causes intense venospasm (FIG. 2). Research suggests that this thickening of the vein wall reduces penetration of the sclerosant thus reducing its efficacy in thick walled veins.

Figure 3:
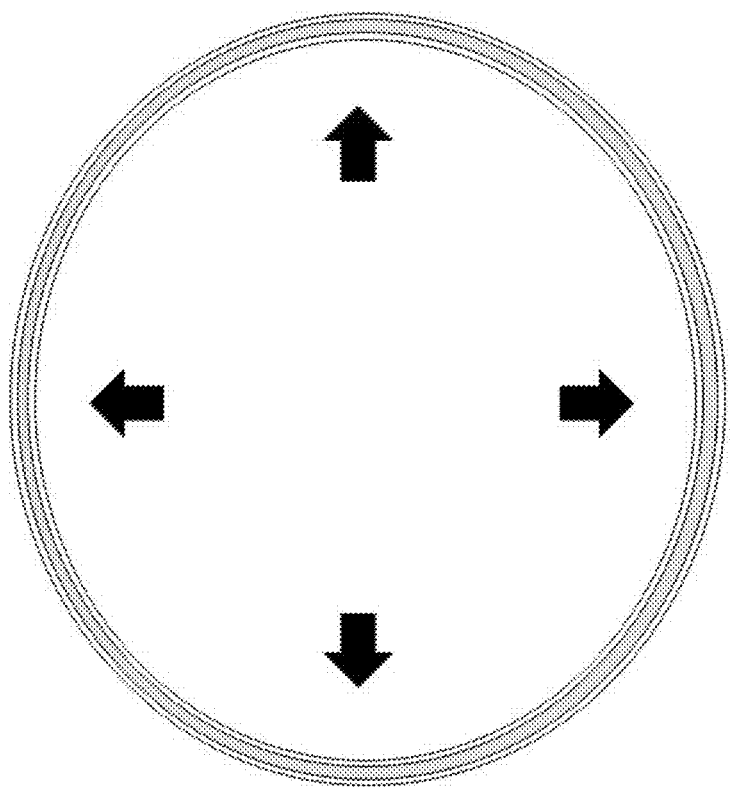
Figure 3:
Figure 3:
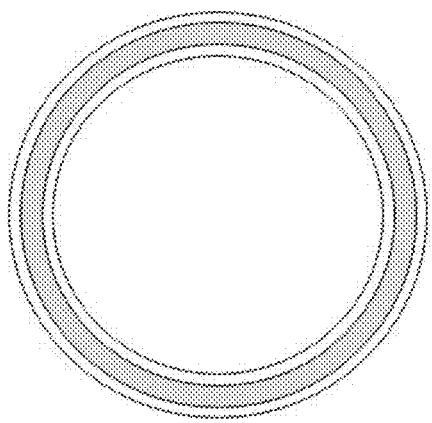

Devices are known that dilate the vein radially (e.g. the "Tulip Tipped" laser) and so reduce the thickness of the vein wall during treatment. However these devices have the disadvantage of increasing the venous lumen, thus filling the vein with blood or tumescence which can then impede the ablative energy or chemical from reaching the vein wall (FIG. 3). Further, increased blood flow to the treatment site also has the potential disadvantage of the treatment agent entering the circulation and having detrimental physiological effects. Indeed, leakage of sclerosants or gas into the circulation should be avoided to reduce the risks of free sclerosant reaching the lungs and gas bubbles reaching the brain leading to potential harmful side effects.

Therefore, herein we disclose an Endovenous (catheter) device for treating a vein that equips the user with the ability to selectively dilate and stretch the lumen of the vessel along one axis only. This, advantageously, counteracts any contraction and thickening of the vessel wall and permits improved delivery of ablating energy or sclerosant into all layers of the vein wall rather than just the adjacent lumen. Without wishing to be bound by theory, we consider it is not only the size of the vein that is important in treatment but also the thickness of the vein wall. Thus by stretching the vein maximally along one axis the vein wall is thinned, improving the efficacy of any ablative therapy by making a transmural effect as easy to achieve as possible.

Additionally, the surface area of the vein wall is also maximised, facilitating any ablative or gluing process. Moreover, despite stretching, the lumen of the vessel is kept as small as possible, thus reducing the volume of blood or any other fluid that might act as a barrier to treatment of the vein wall. This also reduces the volume of sclerosant, glue or other substance needed to fill the lumen during treatment. It also safeguards against leakage of sclerosants or gas into the circulation, reducing the risks of free sclerosant reaching the lungs and gas bubbles reaching the brain with their potential harmful effects. In a similar way, stretching the vessel wall along a single axis whilst minimising the corresponding size of the lumen volume, facilitates the introduction and penetration of local anaesthetic into the stretched vessel thus ensuring the lowest volume of anaesthetic is used to achieve its effect and minimising the risk of any escaping into the circulation.

STATEMENTS OF INVENTION

According to a first aspect of the invention there is provided a medical device for treating a vein comprising:
an elongate member adapted to be inserted into a vein and having, at a first end, a manipulating region and, at a second end, a delivery member for delivering treatment agent to a vein wall;
wherein said second end further comprises at least one vein stretching member having one or more projections extending along the longitudinal axis of said elongate member and also extending away from said delivery member and further wherein each one or all of the projections has/have maximum extension along an axis or axes whereby the vein is stretched away from said delivery member along said axis.

Reference herein to extending along the longitudinal axis of said elongate member is reference to the vein stretching member, or the multiple tips thereof, extending along the length of said elongate member or along the same axis but ahead of said elongate member.

Reference herein to treating a vein refers to any treatment wherein the device according to the invention is inserted into a vein typically, but not exclusively, for the ablation, closure, or removal of said vein. As will be appreciated by those skilled in the art, the device is typically used for the treatment of venous insufficiency including, but not limited to, varicose vein treatment or removal. It will be even further apparent to those skilled in the art that the device is used for either cosmetic or medical purposes. Further the device of the invention can be used in humans or animals.

In a preferred embodiment of the invention said treatment agent is a form of treatment energy or treatment chemical.

In yet a further preferred embodiment said treatment energy includes, but is not limited to, laser energy, radiofrequency energy, electrical current, steam, microwave energy or the like. As will be appreciated by those skilled in the art, in this preferred embodiment, energy is delivered to the vein wall resulting, typically, in localized thermal injury causing occlusion of the said vein. Accordingly, in this preferred embodiment, said delivery member is adapted to conduct heat or light energy, for instance, in one embodiment, it comprises a channel for accommodating an optical fibre or a laser beam. In another embodiment said delivery member is made of a conducting material and exposed to a voltage whereby electric current can flow through same and so be used to treat or ablate the vein wall tissue. Ideally, said delivery member comprises at least one electrode.

Additionally or alternatively, according to this further preferred embodiment of the invention, said device comprises at least one energy delivery system in operable communication with said delivery member whereby energy is delivered to said vein via said delivery member. Most ideally, said energy delivering system is an optical fibre, electrical wire, or the like.

In yet a further preferred embodiment of the invention said energy delivery system comprises at least one inner channel within said manipulating region operably coupled to the delivery member. Alternatively, said energy delivery system comprises at least one channel positioned on, or around, the outer surface of said elongate member and covered by suitable insulating means.

Alternatively, in a further preferred embodiment said treatment chemical is any substance, preferably a fluid, that causes damage and cell death. As will be appreciated by those skilled in the art this includes, but is not limited to, sclerosants including sodium tetradecyl sulphate (STS) and polidocanol (POL), hypertonic saline, glycine, chromate, or the like. According to this preferred embodiment, said delivery member comprises at least one open-ended channel in operable communication with a supply of said treatment chemical whereby said chemical, in use, is delivered via said channel in said delivery member to the vein wall and so used to treat or ablate the vein wall tissue.

In another preferred embodiment of the invention, said delivery member comprises at least one suction device adapted to be applied to a selected part of a vessel wall in order to reduce the lumen volume and/or to cause temporary adherence of the vessel to the device, particularly the stretching projections.

Reference herein to a vein stretching member is any member shaped and/or configured to contact the wall of a vein to be treated which is used to stretch the vein along an axis or axes.

In a preferred embodiment of the invention, said vein stretching member comprises at least two pairs of wire-like members wherein each pair is spaced, with respect to the other pair, along the longitudinal axis of said elongate member and each wire-like member comprises a vein wall contact tip whereby the vein wall is stretched.

In this preferred embodiment, said vein stretching members can contact multiple points along the blood vessel wall simultaneously stretching same.

Alternatively, and more preferably, said vein stretching member is provided as a single frame arranged about or ahead of the delivery member and adapted for dilating the lumen of said vein along a single axis i.e. the widest part of the frame. As will be appreciated by those skilled in the art, in this preferred arrangement the vein stretching member can be any of shape, size and/or diameter to achieve the desired technical effect, accordingly it can be, but is not limited to, a square, circular, or elliptical frame, whose dimensions correspond to the diameter and length of vein to be treated.

In a preferred embodiment of the invention, said vein stretching member is adapted to be expanded and/or contracted such that when located at, or adjacent to, a region of vein to be treated, said vein stretching member expands to engage said vein wall and, similarly, after treatment is complete it contracts to disengage from said vein wall.

Preferably, said vein stretching member includes a mechanical actuating device which is controlled by a user and so, in one embodiment, said mechanical actuating device is operably linked to said manipulating region whereby a user using said device can initiate activation and expansion of said vein stretching member and/or contraction of said vein stretching member. More preferably said mechanical actuating device comprises suitable actuating features such as a hydraulic control member, ideally, embodying a pump.

Alternatively, said vein stretching member is self-expanding and/or self-contracting. As appreciated by those skilled in the art, this can be achieved by numerous means such as by the application of tension (spring loaded device) or in the form of a stent, or a plurality of constrained stiffened wires which when unconstrained, i.e. at the time of exposure to the target region of a vein to be treated for example by removal of a container that contains same extend outwards along the same axis to contact the inner lumen wall of the vein.

In a further embodiment said vein stretching member is made of shape-memory material, such as but not limited to nitinol or the like.

In yet a further preferred or an alternative embodiment of the invention, said device further comprises, additionally or alternatively, a shield for selectively shielding, wholly or partially, said vein stretching member whereby the degree of shielding prevents said vein stretching member from expanding until located at, or adjacent to, the region of the vein to be treated. As will be appreciated by those skilled in the art, the overall diameter of the delivery member, vein stretching member and/or shield is such that it is still small enough to allow ease of passage through the lumen of the vein to be treated.

In a preferred embodiment said shield is adapted to be retracted/protracted, ideally, incrementally and longitudinally along the length of said elongate member or along the longitudinal axis of said elongate member. As will be appreciated by those skilled in the art, said shield can be positioned in a retracted or protracted manner according to a user's requirements.

Alternatively, said shield can be automatically positioned by a control unit, wherein said control unit comprises one or more switches for retracting and/or protracting said shield. As will be appreciated by those skilled in the art, this will allow the selective control of expansion of said vein stretching member.

In a further preferred embodiment, the projections making up the stretching member are hollow and adapted to deliver fluid such as, but not restricted to, sclerosant or glue, to the vessel wall and lumen ideally at the time the vein is stretched along said one axis. Alternatively, the same hollow nature of the projections is adapted to apply suction pressure thus reducing the size of the lumen of the vessel being stretched and/or causing a temporary adherence of the vessel wall to the vein stretching member.

In an alternative embodiment, the projections making up the stretching member are adapted to transmit thermal energy for ablation. For example, said projections are electrically conductive allowing electrical energy to pass through them and into the vein wall, alternatively, said projections are thermally conductive allowing heat to be passed through them to the vein wall, alternatively again they are hollow to allow steam or another thermally active substance to be passed therethrough or to allow laser energy to be passed therethrough and delivered to the vein wall.

In yet a further preferred embodiment of the invention, said elongate member is between 10-400 cm in length, and more ideally between 35-150 cm in length and more ideally still 45-90 cm in length including every 1 cm increment there between or more ideally 45 cm or 65 cm or 90 cm in length. Typically, said elongate member is a catheter.

Further, according to this preferred further embodiment, said vein stretching member is between 0.1-90.0 cm in length and more ideally between 0.2-25 cm in length and more ideally still 0.5-10 cm in length including every 0.1 cm there between. However, other lengths and dimensions could be used to achieve the desired technical effect according to the invention as disclosed herein, as will be appreciated by those skilled in the art, depending upon the size and/or nature of the vein to be treated. Further, as the purpose of the vein stretching member is to promote treatment of the vein via delivery of treatment agent from said delivery member, preferably, said delivery member is the same length or smaller than the overall length of said vein stretching member and thus the length of vein stretched by same.

In yet a further preferred embodiment of the invention said device comprises a vein stretching member contiguous with said elongate member and/or delivery member. Alternatively said vein stretching member is releasably attached to said elongate member and/or delivery member by means of a friction fit and/or a screw fix or any other suitable means known to those skilled in the art. Ideally, where a screw fix is used the vein stretching tip has an internal thread and said elongate member and/or delivery member a complimentary external thread, or vice versa. More preferably, said vein stretching member is fixed by a friction fit augmented by lock means such as a Luer lock.

In a further preferred embodiment said manipulating region is insulated along a substantial part of its length, ideally by tubing or the use of differentially conducting materials, thereby ensuring energy delivery only occurs from said channel(s).

In a further preferred embodiment of the invention said manipulating region may be fashioned to provide a handle.

In yet a further preferred embodiment of the invention, said manipulating region comprises a plurality of markings and/or indentations to indicate the depth of the device when inserted into the vein such that the position of the delivery member and therefore vein stretching member relative to the vein can be determined.

In a further preferred embodiment of the invention, said device is fabricated from any appropriate surgical grade material, such as plastic, PTFE, optical fibre with covering or any other appropriate material.

In yet a further preferred embodiment of the invention said vein stretching member extends away from the longitudinal axis of said elongate member by an angle between 45° and 90°. Most suitably said angle is between 70° and 90°. Yet more ideally still said angle is between 80° and 90° and in a preferred arrangement is at or about 90°.

It will be apparent to those skilled in the art that the design of the device enables a user to treat a vein (for example ablating or closing damaged veins in the treatment of venous disease such as, but not limited to, varicose veins) by stretching the vein to be treated along an axis or axes to facilitate delivery of treatment agent from said delivery member or through the projection(s) of the vein stretching member(s). This action may be enhanced by suction of the vein wall onto the device or vein stretching member(s). As a consequence cell damage and probably protein damage in the vein wall with subsequent scarring leads to natural removal of said vein by the body.

Once the device is inserted into a vein to be treated the vein stretching member stretches the vessel to be treated. In an alternative embodiment, the vein stretching member is either manipulated or expanded such that said stretching member stretches the vessel to be treated. Moreover, as the vein stretching member is more visible by imaging, such as ultrasound, said member can be precisely delineated by imaging. In this arrangement, the vessel wall is stretched maximally to promote delivery of treatment agent to all layers of same, whilst minimising the size of the vessel lumen. The user is then able to deliver treatment agent, such as sclerosant, glue or energy such as laser energy, radiofrequency, electrical current, steam, microwave or the like, causing cell death and/or protein damage deep within said vein wall resulting in occlusion of the vessel. By using differing lengths or arrangements of the vein stretching member(s) as herein described, the user can determine the amount of any stretching and the length of vein wall to be stretched. In this way, the length of the vein ablated can be varied thus permitting treatment of veins having shorter or, alternatively, longer lengths, at any one time. Advantageously, this increases ease of use, accuracy and speed of procedure, and reduces the risk of incomplete ablation. Even more importantly, as will be appreciated by those skilled in the art, the design of the device is such that whilst achieving maximal ablation through stretching of a vein wall, the vein lumen is kept to a minimum avoiding the potential risk of any treatment agent entering the circulation.

According to a second aspect of the invention, there is provided a releasable vein stretching member for attaching to a device for treating a vein, wherein said vein stretching member has one or more projections, in use, extending along the longitudinal axis of said elongate member and also extending away from said delivery member and further wherein each one or all of the projections has/have maximum extension along an axis or axes whereby the vein is stretched axis away from said delivery member along said axis.

According to a further aspect of the invention there is provided a kit of parts for treating a vein comprising:
i) at last one medical device comprising an elongate member adapted to be inserted into a vein and having, at a first end, a manipulating region and, at a second end a delivery member adapted to deliver treatment agent to said vein; and
i) a plurality of releasable vein stretching members having one or more projections, in use, extending along the longitudinal axis of said elongate member and also extending away from said delivery member of said device and further wherein each one or all of the projections has/have maximum extension along an axis or axes whereby the vein is stretched away from said delivery member along said axis and a releasable attachment member for attaching said vein stretching member to said device.
ii)

In this preferred embodiment of the invention, ideally, said vein stretching members are of different sizes and/or shapes and so of different diameters and/or lengths as herein described. Thus the range of vein stretching members will allow the dilation of different diameter and/or length veins.

According to a further aspect of the invention there is provided a method for treating a vein comprising:
a) inserting an elongate member having, at a first end, a manipulating region and, at a second end, a delivery member for delivering treatment agent to a vein wall; wherein said second end further comprises at least one vein stretching member having one or more projections extending along the longitudinal axis of said elongate member and also extending away from said delivery member and further wherein each one or all of the projections has/have maximum extension along an axis or axes whereby the lumen of the vein is stretched away from said delivery member along said axis;
b) positioning said vein stretching member adjacent to a region of said vein to be treated;
c) delivering treatment agent via said delivery member to the vein wall;
d) repositioning said stretching member;
e) optionally, repeating steps c)-d); and
f) withdrawing said device from said vein.

Preferably, said vein stretching member is mechanically controlled by a user. Alternatively, said vein stretching member is operably coupled to a trigger for manipulating or expanding said vein stretching member.

Alternatively still, in a preferred method said vein stretching member is self-expanding. As appreciated by those skilled in the art, this can be achieved by numerous means such as by the provision of a stent, or a plurality of stiffened wires which, when exposed to the target region of the vein extend outwards along the same axis to contact the inner lumen wall of the vein.

In a preferred method of the invention said vein stretching member is expanded by use of a shield.

Most preferably, said device is used to remove damaged veins in the treatment of venous disease such as, but not limited to, varicose veins.

Preferably, the vessel can be anaesthetised when stretched and before treatment by passing local anaesthetic along the device and into the stretched lumen.

Most preferably, said device is used to close or remove blood vessels in the leg but it can also be used in other areas where veins are required to be closed or removed for medical or cosmetic reasons.

Any of the aforementioned aspects of the invention may, in preferred embodiments, include or be characterised by any of the aforementioned features pertaining to the device or the tips. Thus, preferred features of each aspect of the invention may be as described in connection with any of the other aspects.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings).

Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Figure 4:
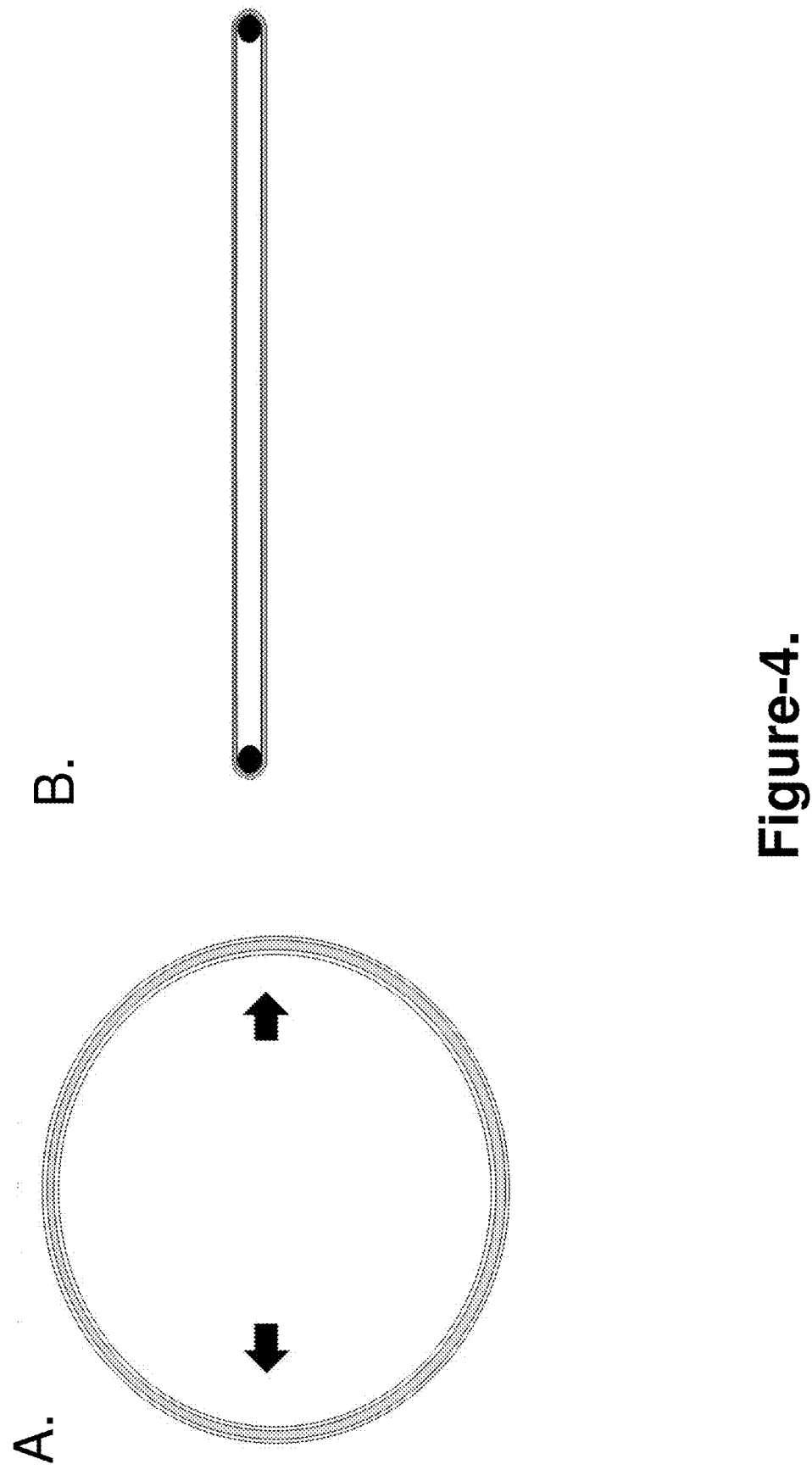
Figure 5:
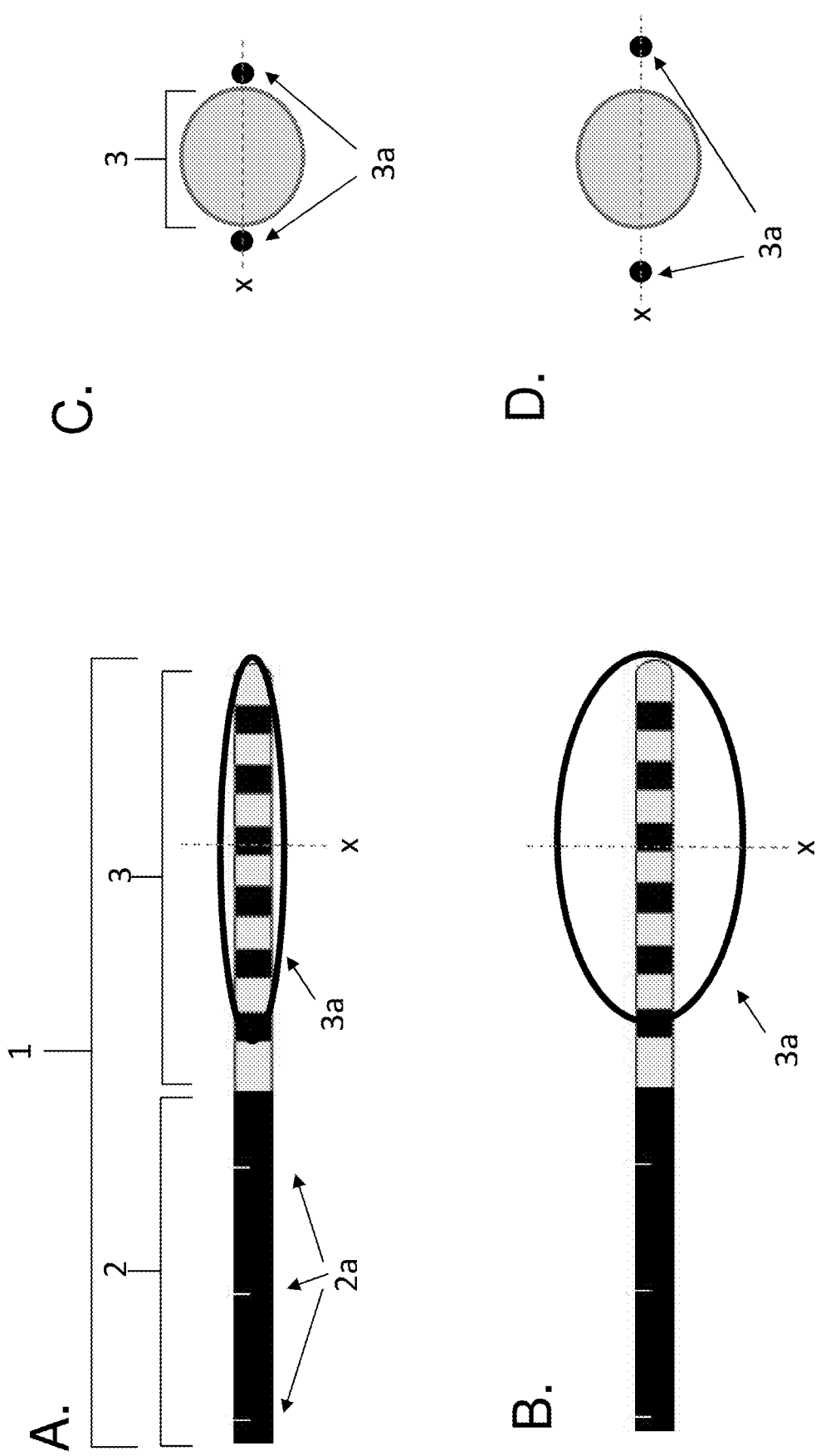
Figure 6:
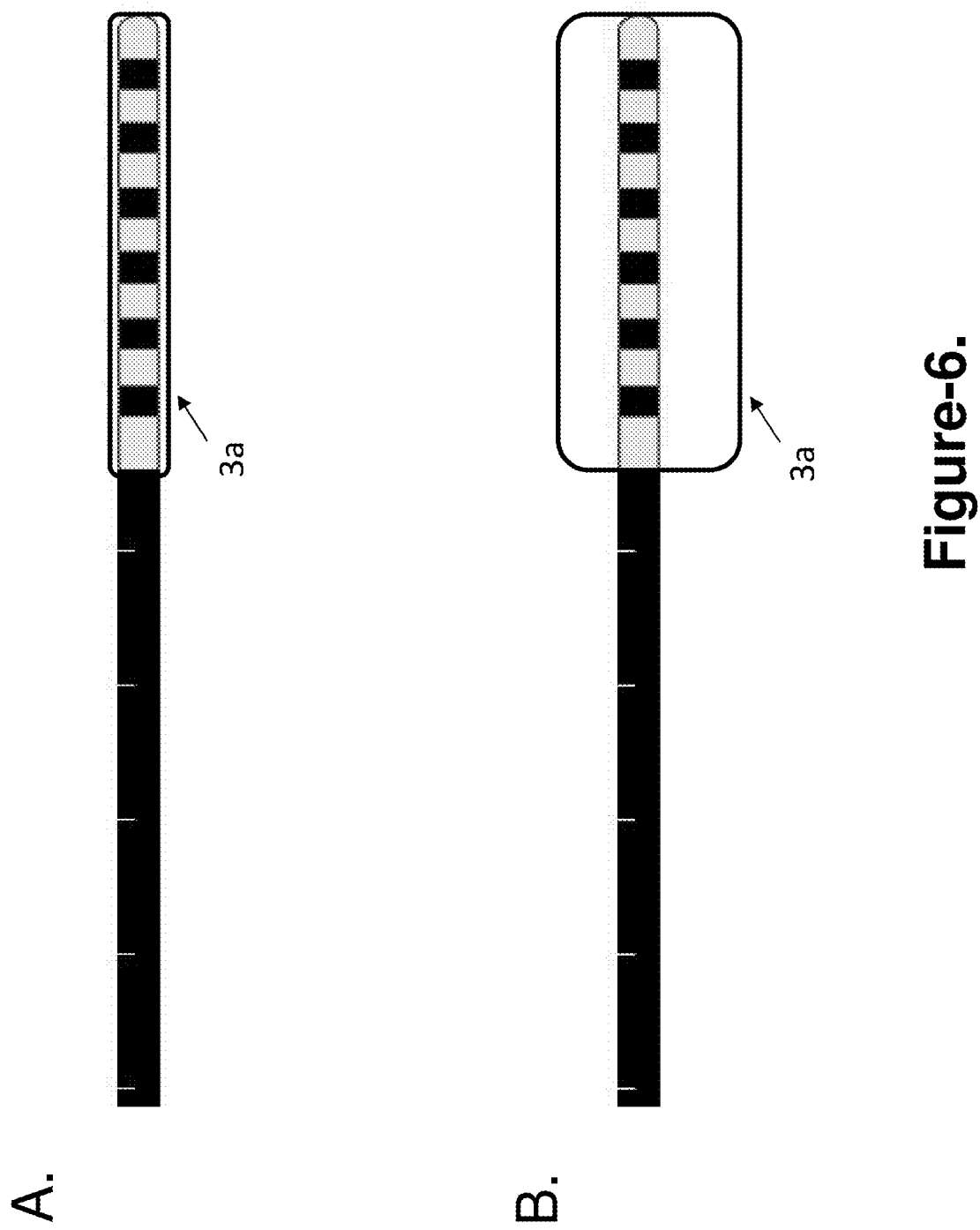
Figure 7:
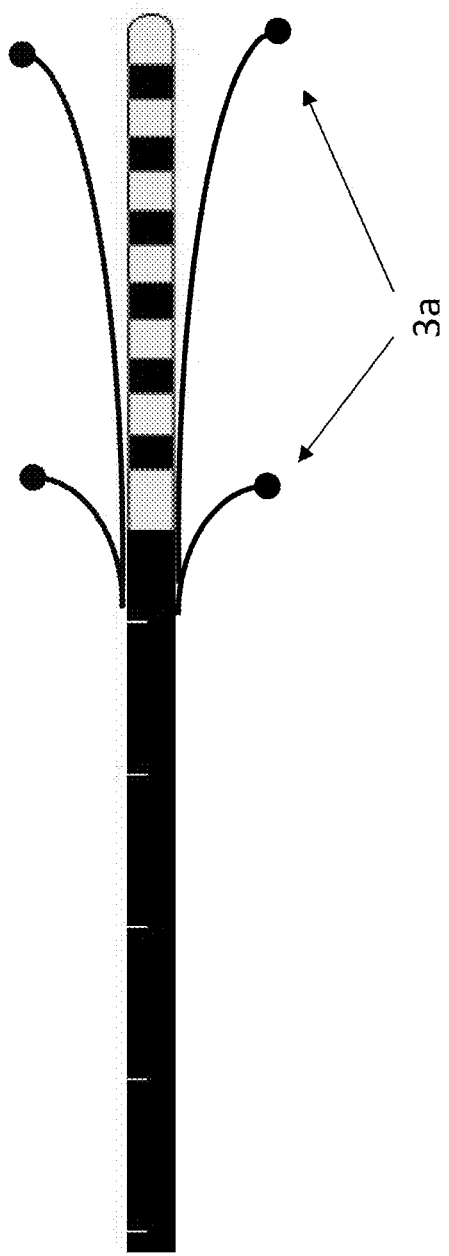
Figure 8:
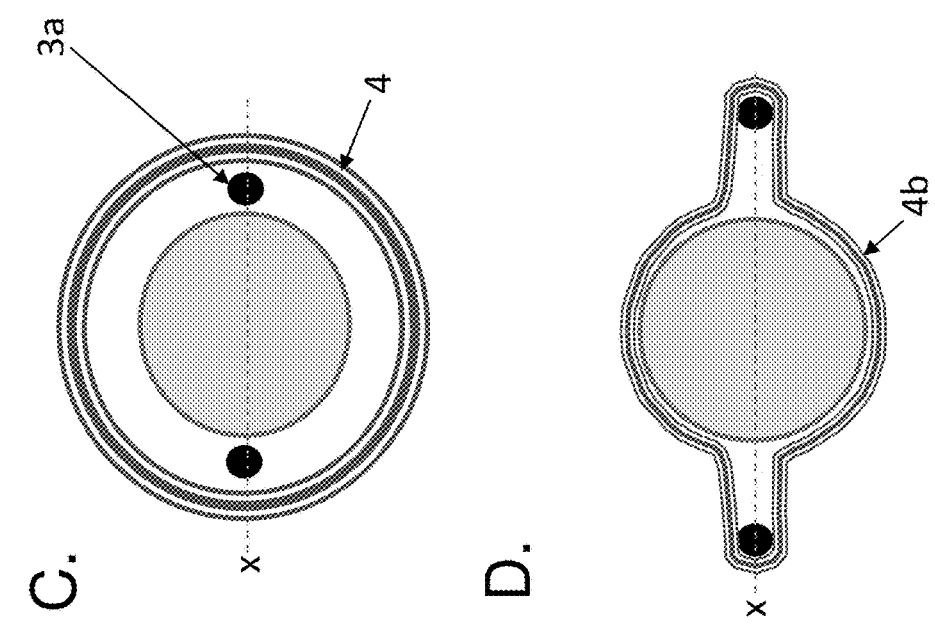
Figure 8:
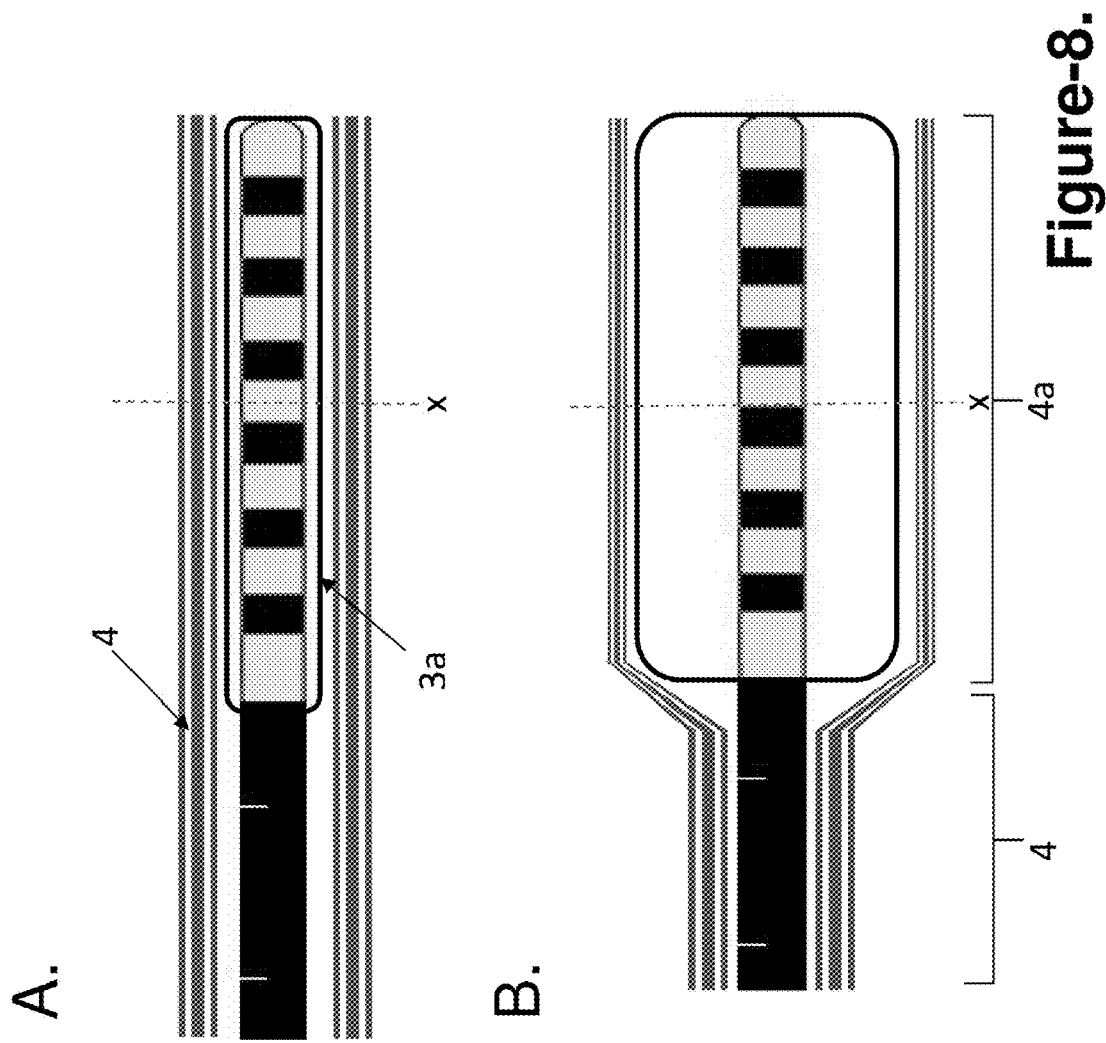
Figure 9:
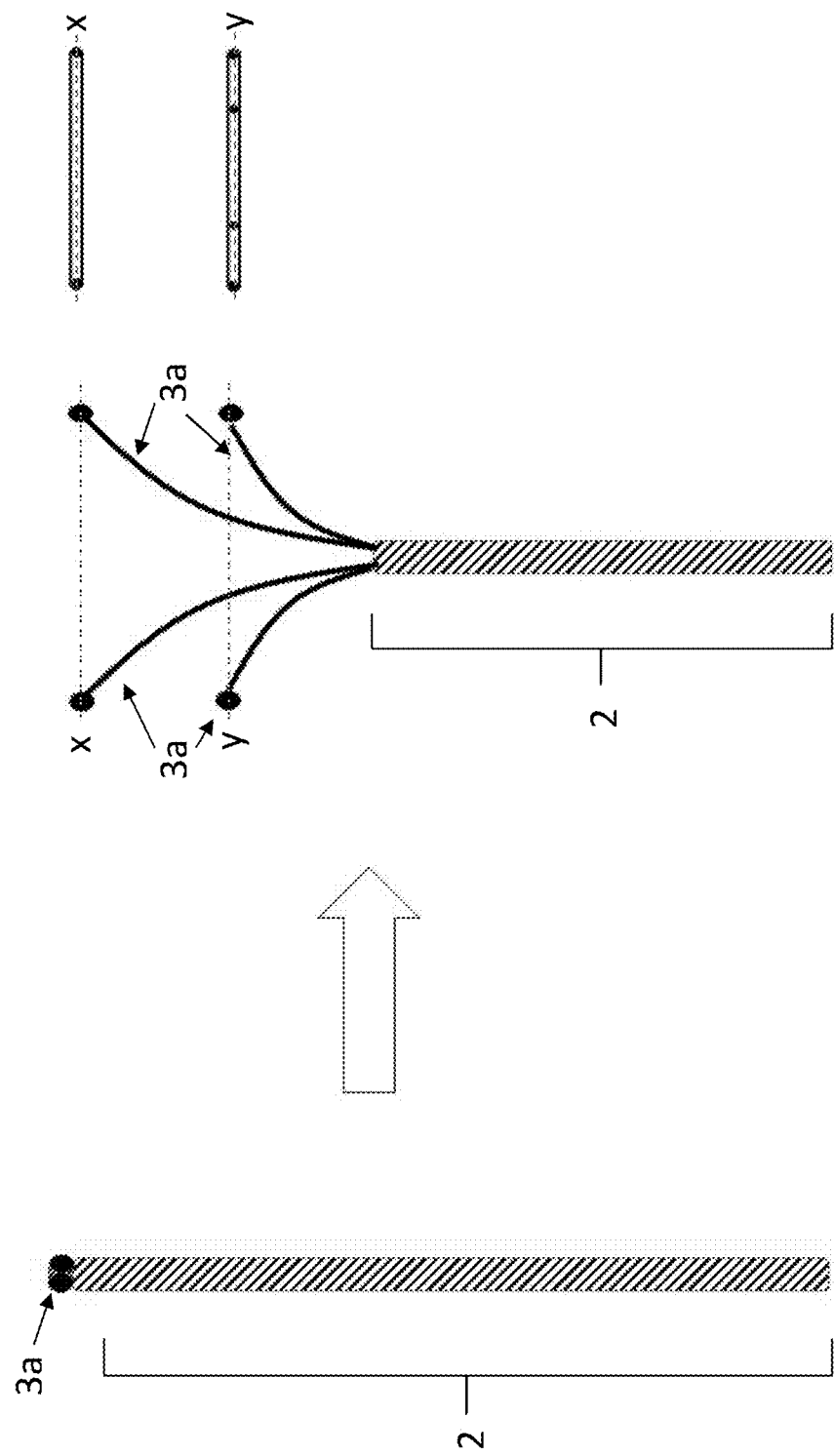
Figure 10:
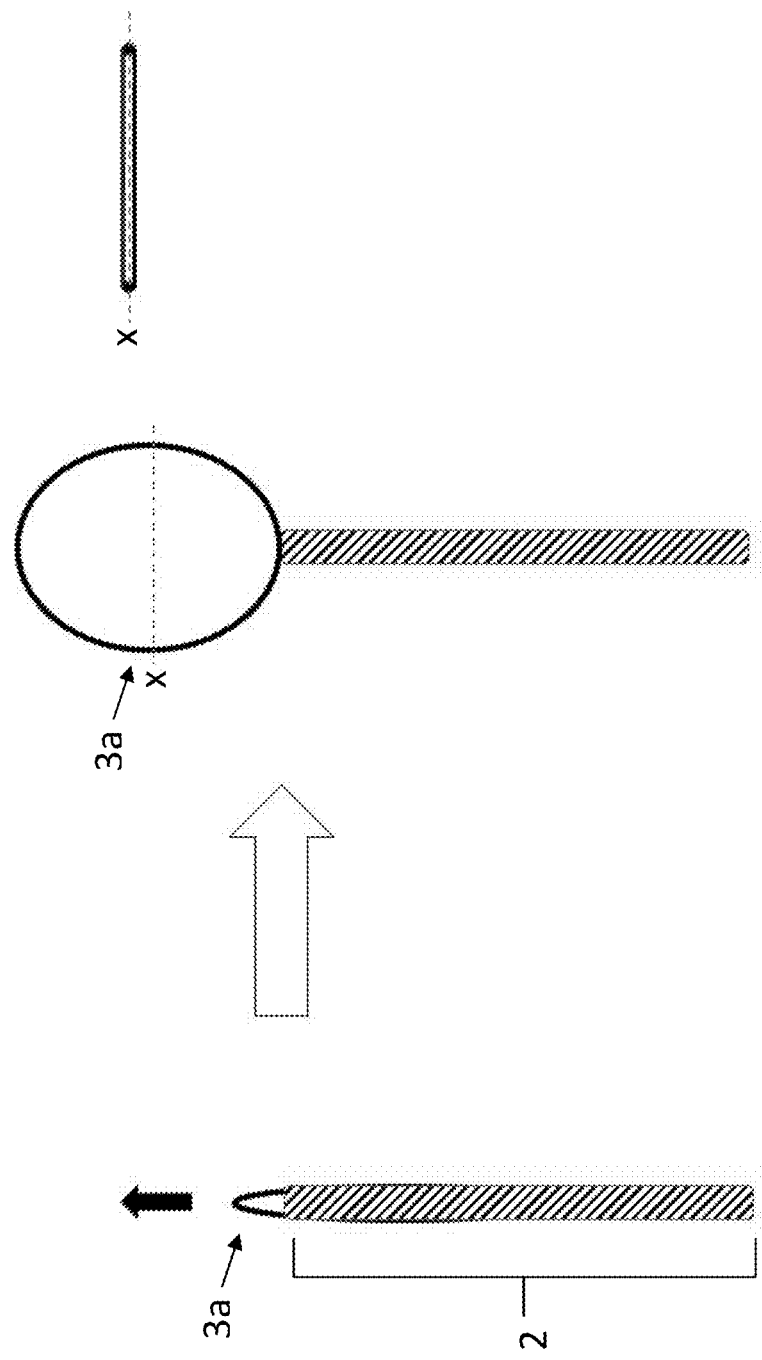

The present invention will now be described by way of example only with particular reference to the following figures wherein:

FIG. 1. A diagrammatic view of a longitudinal and transverse cross-section of a vein to be treated including the different tissue layers comprising the walls of same;

FIG. 2. A diagrammatic view of a transverse cross-section of a vein before and undergoing treatment by endovenous surgery. Upon delivery of tumescence, and also as a result of the pressure and temperature in the case of thermoablation, the vein undergoes constriction leading to a thickening of the venous wall. Similarly, in the case of sclerosants, when injected into the vessel venospasm can result leading to contraction. In totality, this thickening of the vessel wall can reduce efficacy of conduction of treatment agent;

FIG. 3. A diagrammatic view of a transverse cross-section of a vein before and undergoing treatment with radially expanding devices of the prior art. Radial dilation of the vein leads to thinning of the vessel wall to promote delivery of effective treatment, however, the increase in the size of the venous lumen can lead to filling of the vein with blood and/or tumescence which can impede delivery of treatment agent to the vein wall;

FIG. 4. A diagrammatic view of a transverse cross-section of a vein before and undergoing treatment with the device according to the invention. The device is configured such that the vein is dilated along a single axis such that the vein wall is stretched to result in wall thinning, but advantageously the lumen of the vessel remains at a minimum. This improves the efficacy of therapy by making delivery of treatment agent to the entire vessel wall as easy to achieve as possible;

FIG. 5. [A] A side elevation view of a device in accordance with the invention 1. 2 shows the elongate member comprising a number of markings and/or indentations 2a to aid visualisation of the passage of the device. 3 shows the delivery member comprising a vein stretching member 3a, in a closed configuration adapted for delivery and passage into the lumen of the vessel to be treated. [B] A side elevation of a device according to the invention wherein vein stretching member is in an open configuration. [C] and [D] show transverse cross-sectional views of the device viewed along X as depicted in [A] and [B], respectively;

FIG. 6. A side elevation view of a device in accordance with an alternative embodiment of the invention, wherein the vein stretching member is in a closed [A] and open [B] configuration;

FIG. 7. A side elevation view of a device in accordance with an alternative embodiment of the invention. 3a shows a plurality of vein stretching members in an open configuration;

FIG. 8. [A] A partial side-view of a vein 4 containing a device in accordance with the invention, showing the vein stretching member 3a in a closed configuration to allow easy passage of same. [B] A partial side-view of a vein 4 containing a device in accordance with the invention, showing the vein stretching member 3a in an open configuration resulting in dilation the vein adjacent to the delivery member along axis X leading to thinning of the vessel wall. [C] and [D] show transverse cross-sectional views of the device viewed along X as depicted in [A] and [B], respectively;

FIG. 9. A side elevation view of a device in accordance with an alternative embodiment of the invention. 3a shows a plurality of vein stretching members in an open configuration located ahead of the delivery member;

FIG. 10. A side elevation view of a device in accordance with an alternative embodiment of the invention, wherein the vein stretching member is located at the tip of the delivery member in a closed [A] and open [B] configuration and when in an open configuration is circular in section and located ahead of the delivery member; and FIG. 11. A side elevation view of a device in accordance with an alternative embodiment of the invention, wherein the vein stretching member is located at the tip of the delivery member in a closed [A] and open [B] configuration and when in an open configuration is square in section and located ahead of the delivery member.

Referring to FIG. 5, there is shown a diagrammatic side view of the device according to a preferred embodiment of the invention. The device is generally elongate and its diameter is of a size suitable for insertion into a vein to be treated. The device [1] is elongate and, at a first end, there is provided a manipulating region [2], and at a second end, a delivery member [3] and a vein stretching member [3a]. In this illustration, said manipulating region [2] is contiguous with said delivery member [3] and/or vein stretching member [3a]. In other embodiments (not shown) the delivery member and/or said vein stretching member [3a] is separable from the manipulating region [2] but can be securely fixed thereto prior to use. The provision of a removable vein stretching member [3a] permits the user to utilise a selected type of vein stretching member prior to use (for example for use with different sized veins).

In further embodiments, the manipulating region [2] may comprise a number of markings and/or indentations [2a] to aid visualisation of the passage of the device [1] within the vein when in use, providing the user with an indication of the depth of same with respect to the vein to ensure a correct region of the vein is in contact with the delivery member [3] prior to dilation of the vessel using the vein stretching member [3a]. Additionally, in preferred arrangements the manipulating region comprises insulating material along a substantial part of its length such that, when treatment agent is in the form of energy, energy delivery only occurs via the delivery member [3]. In preferred embodiments, the manipulating region may also be fashioned to provide a handle (not shown), to aid handling and use of the device.

At a second end of the device there is delivery member [3], and one or more vein stretching members [3a] which in use engage and stretch the vein wall along axis x. As known to those in the art, a number of different treatment agents can be used with the aim of causing cell death to the vein wall and subsequent occlusion of the blood vessel, such as use of sclerosants or energy in the form of laser energy, radiofrequency, electrical current, steam, or microwave. As will be appreciated by those skilled in the art, and disclosed herein, depending upon the nature of the treatment agent to be delivered, the vein stretching member of delivery member [3] may take various forms (not shown), such as an open-ended channel for delivery of sclerosant, a conducing material including an electrode for delivery of electricity, or adapted for a laser port for delivery of laser energy.

In the FIG. 5 embodiment, a single vein stretching member is illustrated in the form of an elliptical frame, although, stretching members of different sizes and or shapes may be used (such as shown in FIGS. 6 and 7). In this arrangement, the vein stretching member is adapted to expand using conventional means and so after the device has been inserted into the vein, the vein stretching member is expanded outwards to contact the inner vein wall at its widest point. This then effectively allows the user to stretch the vein at a site adjacent to the delivery member to allow maximal thinning of the vessel wall to improve efficacy of treatment agent delivery, whilst effectively minimally expanding the lumen of the vessel. As will be appreciated by those skilled in the art, depending upon the length and diameter of the vein stretching member, the operator can treat different diameter and lengths of vein.

The vein stretching member [3a] is expandable. This adaption for expansion may be in the form of an expandable frame, which under a user's control, can be mechanically moved outwardly and so effectively expanded. Alternatively, the vein stretching member may be held under tension and so is in the form of a self-expanding frame wherein when exposed to the vein to be treated, said tension is released and said frame self-expands outwards to contact the surface of the vein (not shown).

Alternatively, as shown in FIG. 7 said vein stretching member may take the form of a pair of wire-like members each comprising a vein wall contact tip extending outwards along the same axis. Ideally, the contact tips sit along an axis that is at right angles to the longitudinal axis of the elongate member.

In this figure, two vein stretching members or pairs of wires are shown. They are spaced along the longitudinal axis of the elongate member. In each case the contact tips of each pair sit along an axis that is at right angles to the longitudinal axis of the elongate member.

Alternatively, said device may comprise a plurality of vein stretching members each comprising a pair of wire like-members and each having vein wall contact tips wherein the vein wall contact tips of each vein stretching member is spaced longitudinally along the length of said delivery member. Thus, each vein stretching member contacts the vein at different points along the blood vessel wall. Preferably, the ends of the wires are of a nature and arrangement that maximises force that can be applied to the vessel wall whilst minimising the risk of puncturing or piercing same.

The effective delivery of treatment agent is best viewed with regards to FIG. 8. FIG. 8a illustrates a section of a vein [4] to be treated with the device according to the invention inserted therein. The vein stretching member is in a contracted or unexpanded form. As will be appreciated, the overall diameter of the delivery member and vein stretching member is such that it is still small enough to be passed through the vein (FIG. 8c). Once in place, the vein stretching member is expanded such that said member comes into contact with the vein wall and stretches same. This adaption for expansion may be in the form of an expandable frame, which is under a user's control, and so it can be mechanically moved into an expanded position. Alternatively, the vein stretching member may be held under tension and so in the form of a self-expanding frame wherein once the tension is removed (typically when positioned at the site of the vein to be treated) said frame extends outwards to contact the surface of the vein (not shown). Upon doing so, the vessel wall is maximally stretched, thinning same which allows the effective delivery of treatment agent to all layers of the vein wall. Consequently, the device according to the invention permits the vein wall to be deeply treated and counteracts the contraction and thickening of the vessel wall that can occur upon ablation. Indeed, treatment agent is delivered across the entire wall of the vein via the delivery member [3], permitting targeting of the cells across the entire wall of the vein [6]. As will be appreciated by those skilled in the art, this provides more effective cell death, and increased success rates for vein closure. Further, advantageously as depicted in FIGS. 8b and 8d, the lumen of the vessel upon dilation is however kept to a minimum.

According to further preferred embodiments, the device may also comprise a shield (not shown), which may be located over a substantial part of the device including the vein stretching member [3a]. In this way, the degree of shielding determines the expansion of the vein stretching member through retraction of the shield. This retraction/protraction of the shield can be controlled either manually by the user or automatically by a control unit (not shown). Although not shown, said vein stretching member may be biased, typically using a spring, such that once the shield is retracted the tip is expanded thus forcing the vein stretching member to contact the vein wall and stretch same. Then, via the delivery member, a user delivers treatment agent to the stretched wall of the vein and can treat a desired amount of tissue in the region thereof. Alternatively, said vein stretching member includes a mechanical actuating device which is controlled by a user who can initiate activation and expansion of said vein stretching member. In this manner, the user can more carefully control expansion, and therefore, dilation and stretching of the vein.

In FIG. 9 there is shown yet a further embodiment of the invention where a plurality of vein stretching members are located at the tip of the delivery member but in a contracted state. Once in position the vein stretching members are activated and so expanded. In this embodiment the vein stretching member comprises a number of pairs of wire-like structures that extend forwardly and laterally thus effectively stretching the vein wall in a region ahead of the delivery member and so away from the treatment site. Never the less, the tips of each pair of wire-like structures extend along a single axis x-y which is the axis that the vein wall is stretched along. In this embodiment the axis the vein wall is stretched along is at 90° to the longitudinal axis of the device.

In FIG. 10 there is shown yet a further embodiment of the invention where the vein stretching member is located at the tip of the delivery member but in a contracted state. Once in position the vein stretching member is activated and so expanded. In this embodiment the vein stretching member comprises a circular frame that extends forwardly and laterally thus effectively stretching the vein wall at the frame's widest point in a region ahead of the delivery member and so away from the treatment site. Never the less, the frame at its widest point extends along a single axis x which is the axis that the vein wall is stretched along.

Figure 11:
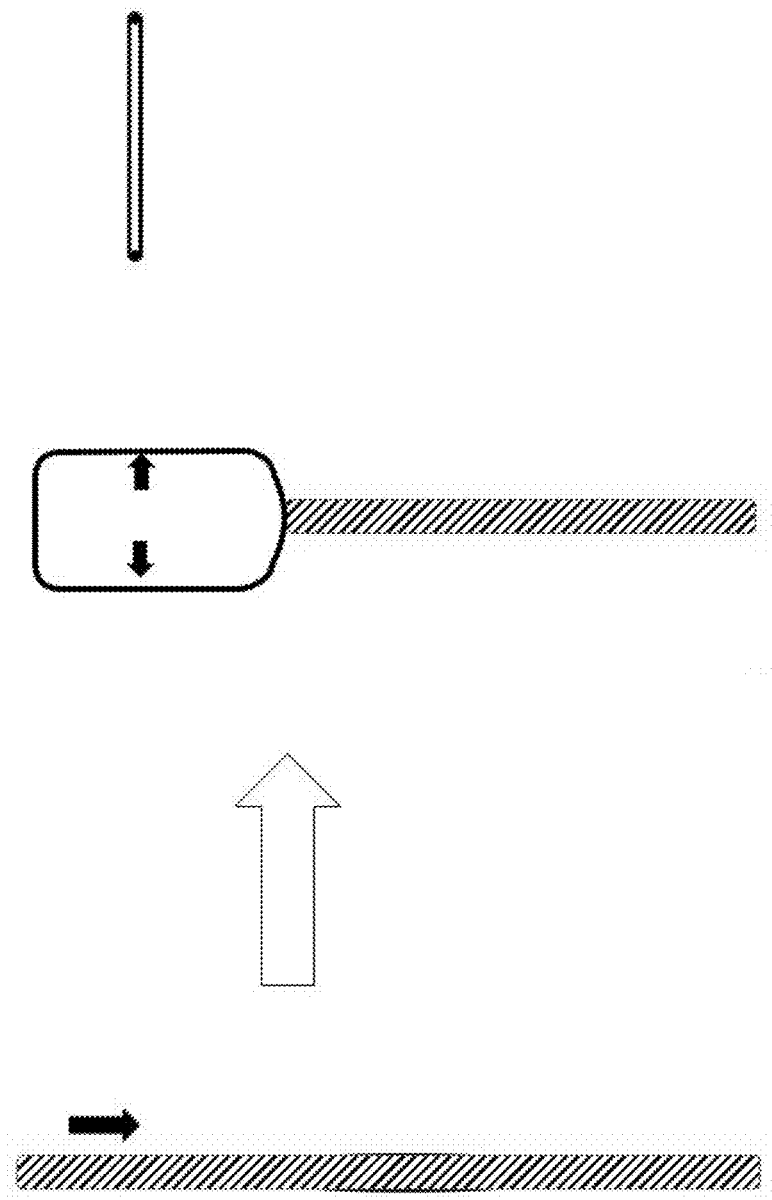

In FIG. 11 there is shown yet a further embodiment of the invention where the vein stretching member is located at the tip of the delivery member but in a contracted state. Once in position the vein stretching member is activated and so expanded. In this embodiment the vein stretching member comprises a square-sectioned frame that extends forwardly and laterally thus effectively stretching the vein wall at the frame's widest point in a region ahead of the delivery member and so away from the treatment site. Never the less, the frame at its widest point extends along a single axis which is the axis that the vein wall is stretched along.

Use of the device as afore described enables the user to dilate the vein along one axis only to allow treatment and permitting the advantages described herein.

What is claimed is:

1. A medical device for treating a vein comprising:
an elongate member adapted to be inserted into a vein and having, at a first end, a manipulating region and, at a second end, a delivery member for delivering treatment agent to a vein wall; wherein said second end further comprises a vein stretching member, wherein said vein stretching member is provided as a frame arranged about or ahead of the delivery member having a maximum extension along a single axis, and wherein said vein stretching member is provided as one of a square, a circular, or an elliptical frame, whereby in use the vein is stretched away from said delivery member in one plane only, minimizing the corresponding size of the lumen volume of the vein.

2. The device according to claim 1, wherein said vein stretching member is adapted to be expanded such that when located at, or adjacent to, the region of the vein to be treated, said vein stretching member is expanded such that it contacts and stretches the blood vessel along said axis, and wherein said vein stretching member comprises a mechanical actuating device operably linked to said manipulating region whereby said actuating device can initiate expansion of said vein stretching member.

3. The device according to claim 1, wherein said vein stretching member is self-expanding.

4. The device according to claim 1, further comprising a shield for selectively shielding, wholly or partially, said vein stretching member, wherein said shield is adapted to be retracted/protracted incrementally and along the length and/or longitudinal axis of said elongate member, and wherein said shield is adapted to be automatically positioned by a control unit, wherein said control unit comprises one or more switches for retracting and/or protracting said shield.

5. The device according to claim 1, wherein said treatment agent is in the form of treatment energy or treatment chemical, wherein said treatment chemical is delivered, in use, to said delivery member via at least one open-ended channel in operable communication with a supply of said treatment chemical and terminating in said delivery member where it is used to treat or ablate the vein wall tissue, wherein said treatment energy is selected from the group comprising: laser energy, radiofrequency, electrical current, steam, or microwave.

6. The device according to claim 1, wherein said vein stretching member is contiguous with said elongate member and/or delivery member.

7. The device according to claim 1, wherein said vein stretching member is releasably attached to said elongate member and/or delivery member.

8. The device according to claim 1, wherein said vein stretching member extends away from the longitudinal axis of said elongate member by an angle between 45° and 90°.

9. A releasable vein stretching member for attaching to a device for treating a vein, wherein said vein stretching member is provided as a frame arranged about or ahead of the delivery member having a maximum extension along a single axis, and wherein said vein stretching member is provided as one of a square, a circular, or an elliptical frame, whereby in use the vein is stretched away from said delivery member in one plane only, minimizing the corresponding size of the lumen volume of the vein.

10. A kit of parts for use with a device for treating a vein comprising:
  i) at least one medical device comprising an elongate member adapted to be inserted into a vein and having, at a first end, a manipulating region and, at a second end a delivery member adapted to deliver treatment agent to said vein; and
  ii) a vein stretching member is provided as a frame arranged about or ahead of the delivery member having a maximum extension along a single axis, and wherein said vein stretching member is provided as one of a square, a circular, or an elliptical frame, whereby in use the vein is stretched away from said delivery member in one plane only, minimizing the corresponding size of the lumen volume of the vein, and further comprising a releasable attachment member for attaching said vein stretching member to said device.

11. A method for treating a vein comprising:
  a) inserting an elongate member having, at a first end, a manipulating region and, at a second end, a delivery member for delivering treatment agent to a vein wall; wherein said second end further comprises a vein stretching member provided as a frame arranged about or ahead of the delivery member having a maximum extension along a single axis, and wherein said vein stretching member is provided as one of a square, a circular, or an elliptical frame, whereby in use the vein is stretched away from said delivery member in one plane only, minimizing the corresponding size of the lumen volume of the vein;
  b) positioning said vein stretching member adjacent to a region of said vein to be treated;
  c) delivering treatment agent via said delivery member to the vein wall;
  d) repositioning said stretching member; and
  e) withdrawing said device from said vein.

12. A method according to claim 11, wherein after b) and before c) said vein stretching member is expanded to make contact with and stretch the vein along said axis, wherein said vein stretching member may be mechanically moved and so expanded by a user, or wherein said vein stretching member is self-expanding under tension.

13. The method of treatment according to claim 11, wherein said vein stretching member is expanded by use of a shield.

14. The method of treatment according to claim 11, wherein said treatment agent is a treatment chemical or treatment energy, optionally wherein said treatment chemical is a sclerosant.

15. The method of treatment according to claim 11, wherein said treatment chemical is a glue or an adhesive substance.

16. The method of treatment according to claim 11, wherein said treatment energy is selected from the group comprising: laser energy, radiofrequency, electrical current, steam, or microwaves.

17. The method of treatment according to claim 11, to treat venous disease.

* * * * *